United States Patent [19]

Yang et al.

[11] 4,329,515

[45] May 11, 1982

[54] CATALYST REMOVAL FROM ALCOHOL ALKOXYLATES

[75] Inventors: Kang Yang; Gerald L. Nield; Paul H. Washecheck, all of Ponca City, Okla.

[73] Assignee: Conoco Inc., Ponca City, Okla.

[21] Appl. No.: 210,994

[22] Filed: Nov. 28, 1980

[51] Int. Cl.$^3$ ............................................. C07C 41/34
[52] U.S. Cl. .................................................... 568/621
[58] Field of Search ......................................... 568/621

[56] References Cited

U.S. PATENT DOCUMENTS

| | | | |
|---|---|---|---|
| 2,983,763 | 5/1961 | Krause | 568/621 X |
| 3,000,963 | 9/1961 | Speranza | 568/621 |
| 3,365,402 | 1/1968 | Brenkman et al. | 568/621 X |
| 4,254,287 | 3/1981 | Ziegenhain et al. | 568/621 |

FOREIGN PATENT DOCUMENTS 1228461  4/1971  United Kingdom ................ 568/621

*Primary Examiner*—Bernard Helfin
*Attorney, Agent, or Firm*—Cortlan R. Schupbach, Jr.

[57] ABSTRACT

Basic compounds of Ba and Sr used in the production of peaked alcohol alkoxylates can be removed from the products by precipitating with some polybasic organic acids. Examples of effective acids include glutaric, diglycolic, adipic, and azelaic acids.

1 Claim, No Drawings

CATALYST REMOVAL FROM ALCOHOL ALKOXYLATES

This invention relates to a method for removing basic barium and strontium-containing catalysts from alcohol ethoxylates produced using those catalysts. More specifically, this invention relates to a method for removing such catalysts by using effective dibasic and polybasic organic acids.

The removal of metal-containing catalysts from reaction products is in general well known and is illustrated by U.S. Pat. Nos. 4,129,718; 3,030,426; 3,000,963; 3,328,306 and 2,983,763. However these references all teach the removal of such metals by simple neutralization with an acid to form an insoluble precipitate which is then removed from the reaction product. However, these methods are not totally effective with barium-containing and strontium-containing catalysts, since it is necessary with certain metals to remove substantially all such metals from the reaction product. Normally, such metals must be removed to at least below about 30 to 40 parts per million, and preferably below about 10 parts per million by weight based upon the weight of the reaction product.

We have discovered that barium and strontium catalysts can be used to produce a peaked alkoxylation product from the alkoxylation of alcohols. However, these metals are present after the reaction in large concentrations, sometimes approaching 1000 parts per million by weight. It is desirable to reduce the metal content to as low a level as possible, resulting in the preferential substantial absence of these metals from reaction products. The normally used mineral acids are not effective in reducing these metals to the desired low levels.

It would be of great benefit to provide a method whereby the barium and/or strontium content of alcohol ethoxylates produced using these catalysts can be reduced to below 40 parts per million by weight. The process used should be complete in one pass, relatively inexpensive, and result in an alcohol alkoxylate substantially free of barium and/or strontium while maintaining normal alkoxylate characteristics.

It has now been discovered according to the present invention that basic barium-containing and strontium-containing catalysts can be removed from alcohol ethoxylate products by adding at least a stoichiometric amount, based upon the catalyst present, of a dibasic or polybasic organic acid, allowing an insoluble barium-containing and/or strontium-containing precipitate to form and then separating the precipitate from the alcohol alkoxylates.

In carrying out the process of the instant invention, alkoxylates are produced by contacting an alcohol with an alkoxylating agent, normally ethylene oxide, in the presence of a basic barium-containing or strontium-containing catalyst. For pratical purposes from about 0.05 to about 5 weight percent of these basic catalysts, based upon the weight of the alcohol to be reacted, is present in the reaction.

Representative examples of such alcohols are those derived by hydrogenation of natrual fats and oils, such as CO and TA alcohols, trademark of and sold by Procter and Gamble Co., such as CO-1214N alcohol, CO 1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be ethoxylated. Examples of these alcohols are ALFOL alcohols, trademark of and sold by Conoco Inc. such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohols, trademark of and sold by Shell Oil Co., such as NEODOL 23 alcohol, NEODOL 25 alcohol, NEODOL 45 alcohol; TERGITOL-L alcohols, trademark of Union Carbide Corp., such as TERGITOL-L 125 alcohol; LIAL alcohols, trademark of and sold by Liquichimica Co. such as LIAL 125; and isodecyl and tridecyl alcohols, sold by Exxon Corp., such as isodecyl alcohol and tridecyl alcohol. Guerbet alcohols can also be ethoxylated. Representative examples of these alcohols are STANDAMUL alcohols, trademark of and sold by Henkel Chemical Co., such as STANDAMUL GT-12 alcohol, STANDAMUL GT-16 alcohol, STANDAMUL GT-20 alcohol, STANDAMUL GT-1620 alcohol. Secondary alcohols can also be used, such as TERGITOL 15 alcohol, trademark of and sold by Union Carbide Corp.

Representative examples of such alcohols are 1-decanol; 1-undecanol; 1-dodecanol; 1-tridecanol; 1-tetradecanol; 1-pentadecanol; 1-hexadecanol; 1-heptadecanol; 1-octadecanol; 1-nonadecanol; 1-eicosanol; 1-docosanol; 2-methyl-1-undecanol; 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadecenol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol; tetracosanol; hexacosanol; octacosanol; triacontanol; dotriacontanol; 2-tetradecyloctadecanol; 2-hexadecyleicosanol.

While any alkylene oxide can be used as an alkoxylating agent, normally ethylene oxide or propylene oxide is used, and of these, ethylene oxide is by far the most commonly used commercial adduct. Generally, the treatment of alcohol with ethylene oxide yields a nonionic detergent, since hydrogen bonding to numerous oxygen molecules makes the polyether end of the molecule water soluble. Alternatively, the ethoxylates can be converted into sulfates and used in the form of alkali metal salts. These processes produce products with only small amounts of side products, sharp adduct distributions and which have improved physical properties over prior art methods. However, for many uses barium and strontium catalysts should be removed. For example, these catalysts should be removed before ether sulfates are produced from these ethoxylates.

In carrying out the catalyst removal taught in the present invention, preferred acids are dibasic organic acids having the general formula $$HO_2C(X)CO_2H,$$

wherein X is the total number of carbon and oxygen atoms present in the molecular chain of the dibasic acid and wherein the total number of carbon and oxygen atoms represented by X is from 0 to 12. Normally, such dibasic acids will have an X value of from 1 to 12, more commonly from 1 to 8. However, other polybasic acids also reduce metal content of alcohol alkoxylates from reaction levels.

These polybasic acids are added to the alkoxylate product containing the basic barium or strontium catalysts in an amount to reduce metal levels. Generally, but not critically, these acids are used in at least a stoichiometric amount. However, it is preferred to use a stoichiometric excess of about 10%. Common usage would require from about 10% to 100% stoichiometric excess over the calculated amount of catalyst in the alkoxylated product. Such excess of acid in no way is detrimental to the alkoxylated product, since the relative amount of the acids added is small compared to the volume of the product as a whole. The acids themselves are weakly acidic, few having a pH of less than 5. In addition, the alkoxylated product itself is a buffering agent tending to maintain the pH of the solution, yielding a substantially neutral value of 6.5 to 7.5.

Temperature is not critical to the present invention other than using a temperature in the range not detrimental to the alkoxylated products. Normally, the dibasic or polybasic acids will be added in the neutralization reaction at a temperature of from about 0° C. to about 150° C, but temperatures of from about 20° C. to about 100° C. are preferred. Pressure is not critical.

After the acids have been added to the alkoxylated product and reaction with the catalyst residues has occurred, a precipitate will form. This precipitate is insoluble in the alkoxylated product and can be removed by techniques well known to those skilled in this art such as by filtration or centrifugation.

The process of the instant invention is effective in removing residual barium and/or strontium content of the alkoxylated products to a low level. Many acids reduce metal content to below about 40 parts per million, and in most cases well below about 10 parts per million. Such levels of metal constitute a substantially complete removal.

The instant invention is more concretely described with reference to the examples below wherein all parts and percentages are by weight unless otherwise specified. The examples are provided to illustrate the present invention and not to limit it.

EXAMPLE 1

Strontium catalysts were prepared by mixing 5.0 grams strontium hydroxide octahydrate, 3.3 grams of phenol and 8.9 grams of water. After 30 minutes agitation, solid residue was discarded by filtration. A 600 milliliter (ml) stainless steel reactor was charged with 120 grams of ALFOL 1214 alcohol (trademark of and sold by Conoco Inc. a 12 to 14 carbon atom paraffinic alcohol) and 1.6 grams of catalyst. The reactants were heated to 178° C. under continuous purge with nitrogen at 500 cubic centimeters (cc)/per minute. After brief evacuation, ethylene oxide was charged to a pressure of 40 pounds per square inch gauge (psig). Thereafter, 150 grams of ethylene oxide (EO) was allowed to react over a 90 minute period.

After reaction the product was analyzed for strontium content. Strontium content was approximately 700 ppm. The product was cooled to 50° C. and the catalyst was neutralized with 110% stoichiometric amount of azelaic acid. Precipitate formed, which was removed by centrifugation. The centrifuged product contained only 10.3 parts per million (ppm) strontium.

COMPARATIVE EXAMPLE 2

Experiments were carried out exactly as described in Example 1 except that neutralization was attempted with 2-ethylhexanoic acid. Residual strontium after centrifugation exceeded 100 ppm but was less than the starting solution.

COMPARATIVE EXAMPLE 3

Experiments were carried out exactly as described in Example 1 except that neutralization was attempted with acetic anhydride. Residual strontium content after centrifugation exceeded 100 ppm but was less than the starting solution.

COMPARATIVE EXAMPLE 4

Experiments were carried out excactly as described in Example except that concentrated sulfuric acid was used to neutralize the strontium catalyst. After centrifugation, the residual strontium content exceeded 100 ppm but was less than the starting solution.

COMPARATIVE EXAMPLE 5

Experiments were carried out exactly as described in Example 1 except that concentrated phosphoric acid was used to neutralize the catalyst. After centrifugation residual strontium content exceeded 100 ppm but was less than the starting solution.

COMPARATIVE EXAMPLE 6

An experiment was carried out exactly as described in Example 1 except that paratoluene sulfonic acid was used to neutralize the catalyst. After centrifugation strontium content exceeded 100 ppm but was less than the starting solution.

EXAMPLE 7

An experiment was carried out as described in Example 1 except that adipic acid was used to neutralize the catalyst. The centrifuged product containing only 9.4 ppm strontium.

EXAMPLE 8

An experiment was carried out as described in Example 1 using 184 grams ALFOL 1412 alcohol and 0.3 grams barium hydroxide monohydrate. 120 grams of ethylene oxide was allowed to react over an 80 minute period. The product was neutralized with 110% stoichiometric adipic acid at 50° C. A precipitate was formed and centrifuged. The centrifuged alkoxylated product contained 7.3 ppm barium.

EXAMPLE 9

An experiment was carried out as described in Example 8 with diglycolic acid. The residual barium content after centrifugation was 26 ppm.

EXAMPLE 10

An experiment was carried out as described in Example 8 using glutaric acid. After centrifugation the ethoxylate containing 24 ppm residual barium.

COMPARATIVE EXAMPLE 11

An experiment was carried out as described in Example 4 using concentrated sulfuric acid or concentrated phosphoric acid. With barium, erratic results were noted. In most experiments, barium levels were above 50 parts per million with some above 10 ppm. Some residual barium levels were below 50 ppm but exceeded 40 ppm.

EXAMPLE 12

A sample of 12 to 14 carbon atom alcohol ethoxylated to 40% by weight using strontium-containing catalysts was used in an experiment carried out exactly as described in Example 1 except that adipic acid was used to neutralize the catalyst. The sample after neutralization was centrifuged 10 minutes at 8,000 relative centrigural force (RCF) to yield a stronium content as determined by X-ray fluorescence of 11.5 parts per million.

The experiment was repeated exactly except that the centrifuge was continued for 25 minutes at which time the X-ray fluorescence showed a strontium content of 7.8 parts per million.

EXAMPLE 13

The experiment as described in Example 12 was repeated a third time wherein the centrifugation was carried out for 10 minutes at an increased RCF of 10,450 RCF to yield an X-ray fluorescence strontium content of 8.5 parts per million.

In examples 14 through 23 a sample of 12 to 14 carbon atom alcohol ethoxylated to a 60% level by weight was used. Experiments were carried out exactly as described in Example 1 except that centrifugation was carried out for 10 minutes at a RCF of 10,450. The residual strontium content was determined using X-ray fluorescence.

Adipic acid was used to neutralize the catalyst. Under the conditions of the test, residual strontium content was 29.1 parts per million.

EXAMPLE 14

The experiment was carried out as described in Example 1 except that suberic acid was used to neutralize the catalyst. The residual strontium content was 26.3 parts per million.

EXAMPLE 15

The experiment was carried out as described in Example 1 except that sebacic acid was used to neutralize the catalyst. The residual strontium content was 5.7 parts per million.

EXAMPLE 16

The experiment was carried out exactly as described in Example 1 except that citric acid was used in neutralize the catalyst. Residual strontium content was 21.5 parts per million.

EXAMPLE 17

The experiment was carried out exactly as described in Example 1 except that terephthalic acid was used to neutralize the catalyst. Residual strontium content was 109 parts per million.

EXAMPLE 18

The experiment was carried out exactly as described in Example 1 except that isophthalic acid was used to neutralize the catalyst. Residual strontium content was 234 parts per million.

COMPARATIVE EXAMPLE 19

The experiment was carried out exactly as described in Example 1 except that nitrilotriacetic acid was used to neutralize the catalyst. Residual strontium content was 740 parts per million.

EXAMPLE 20

The experiment was carried out exactly as described in Example 1 except that itaconic acid was used to neutralize the catalyst. Residual strontium content was 18 parts per million.

EXAMPLE 21

The experiment was carried out exactly as described in Example 1 except that malic acid was used to neutralize the catalyst. Residual strontium content was 19 parts per million.

EXAMPLE 22

The experiment was carried out exactly as described in Example 1 except that tartaric acid was used to neutralize the catalyst. Residual strontium content was 25 parts per million.

EXAMPLE 23

The experiment was carried out exactly as described in Example 1 except that malonic acid was used to neutralize the catalyst. Residual strontium metal was 23 parts per million.

In experiments 24 through 32 the same procedure was used as described for experiments 15 through 25 except that the alkoxylated was a 12 to 14 carbon atom alcohol ethoxylated to a 40% level by weight.

EXAMPLE 24

An experiment was carried out as described in Example 1 except that oxalic acid was used. Residual strontium metal was 21 parts per million.

EXAMPLE 25

An experiment was carried out as described in Example 1 except that succinic acid was used. Residual strontium metal was 6.7 parts per million.

EXAMPLE 26

An experiment was carried out as described in Example 1 except that malonic acid was used. Residual strontium content was 8.5 parts per million.

EXAMPLE 27

An experiment was carried out as described in Example 1 except that citric acid was used. Residual strontium content was 24 parts per million.

EXAMPLE 28

An experiment was carried out as described in Example 1 except that malic acid was used. Residual strontium content was 4.6 parts per million.

EXAMPLE 29

An experiment was carried out as described in Example 1 except that fumaric acid was used. Residual strontium content was 27 parts per million.

EXAMPLE 30

An experiment was carried out as described in Example 1 except that maleic acid was used. Residual strontium content was 232 parts per million.

COMPARATIVE EXAMPLE 31

An experiment was carried out as described in Example 1 except that nitrilotriacetic acid was used. Residual strontium content was 883 parts per million.

EXAMPLE 32

An experiment was carried out as described in Example 1 except that phthalic acid was used. Residual strontium content was 38 parts per million.

In general, it is desired to reduce the metal content to below about 60 parts per million and most preferably below about 40 parts per million. Acids efficient for these low levels of removal include azelaic, adipic, diglycolic, glutaric, sebacic, citric, itaconic, malic, tartaric, oxalic, succinic, fumaric, phthalic, suberic, and malonic.

Thus it can be seen that not all polybasic or dibasic organic acids are effective in reducing residual barium and strontium metals to the low levels desired. Mineral acids used in prior art catalyst removal were likewise not effective.

While certain embodiments and details have been shown for the purpose of illustrating this invention, it will be apparent to those skilled in this art that various changes and modifications may be made herein without departing from the spirit or scope of the invention.

We claim:

1. A method for reducing barium containing and strontium containing residues to levels below about 40 parts per million in alcohol alkoxylate products containing said residue, the method comprising
    (a) adding an organic acid selected from the group consisting of glutaric, tartaric, oxalic, succinic, diglycolic, adipic, azelaic, sebasic, citric, itaconic, subseric, malic, malonic and fumaric, or mixtures of these of a temperature of from about 0° C. to about 150° C.;
    (b) allowing an insoluble barium containing or strontium containing percipitate to form, then
    (c) separating the precipitate from the alcohol alkoxylate by filtration, centrifugation or a combination of these.

* * * * *